United States Patent [19]

König et al.

[11] 4,275,001
[45] Jun. 23, 1981

[54] PROCESS FOR THE MANUFACTURE OF LH-RH AND LH-RH ANALOGS USING ⌐GLU-HIS(DNP)-OH

[75] Inventors: Wolfgang König; Volker Teetz, both of Hofheim; Georg Jäger, Bad Soden; Rolf Geiger, Frankfurt, all of Fed. Rep. of Germany

[73] Assignee: Hoechst Aktiengesellschaft, Frankfurt, Fed. Rep. of Germany

[21] Appl. No.: 120,924

[22] Filed: Feb. 12, 1980

[30] Foreign Application Priority Data

Feb. 14, 1979 [DE] Fed. Rep. of Germany ....... 2905502

[51] Int. Cl.$^3$ ........................................... C07C 103/52
[52] U.S. Cl. .................... 260/112.5 LH; 260/112.5 R
[58] Field of Search .............. 260/112.5 R, 112.5 LH; 424/177

[56] References Cited

U.S. PATENT DOCUMENTS 4,083,967  4/1978  Beddell et al. ................ 260/112.5 R Primary Examiner—Delbert R. Phillips
Attorney, Agent, or Firm—Curtis, Morris & Safford

[57] ABSTRACT

What is disclosed is a method for the manufacture of LH-RH and LH-RH analogs, which comprises reacting ⌐Glu-His(DnP)-OH with the corresponding peptide having a free amino group and protected carboxy groups in a solvent as used in peptide chemistry and with the addition of 3-hydroxy-4-oxo-3,4-dihydro-1,2,3-benzotriazine (HOObt) and a carbodiimide and then splitting off the Dnp-(2,4-dinitrophenyl) group. The new method greatly reduces the degree of histidine racemization. The invention also provides a new dipeptide, i.e. ⌐Glu-His(Dnp)-OH.

4 Claims, No Drawings

PROCESS FOR THE MANUFACTURE OF LH-RH AND LH-RH ANALOGS USING ⌐GLU-HIS(DNP)-OH

It is the object of the present invention to provide a process for the manufacture of LH-RH and LH-RH analogs, which comprises reacting Glu-His(Dnp)-OH with the corresponding peptide having a free amino group and protected carboxy groups in a solvent as used in peptide chemistry and with the addition of 3-hydroxy-4-oxo-3,4-dihydro-1,2,3-benzotriazine (HOObt) and a carbodiimide and then splitting off the Dnp-(2,4-dinitrophenyl) group.

It is known that LH-RH is a hormone of the hypothalamus of the formula I

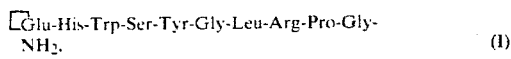
(I)

releasing the gonadotropic hormones LH and FSH in the pituitary gland. LH-RH analogs are peptides in which individual or several amino acids of LH-RH are replaced and/or the peptide chain is modified by shortening, lengthening and/or derivatization. The substitution of glycine in position 6 by D-amino acids and in position 10 by alkyl amines has gained special importance.

Suitable second components in the process of the invention are, therefore, mainly octa- and hepta-peptides of the formulae

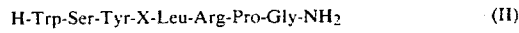
(II)

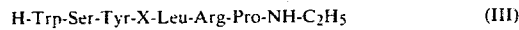
(III)

in which X denotes Gly or D-amino acids or derivatives thereof, for example D-Ser(Bu$^t$), D-Leu, D-Ala, D-Phe, D-Trp, D-Gln(cyclohexyl), D-Glu(OBu$^t$) and D-Lys(-Boc).

The novel dipeptide derivative ⌐Glu-His(Dnp)-OH used as starting component is prepared in usual manner, for example by reacting ⌐Glu-His-OH with 2,4-dinitrofluorobenzene in aqueous solution buffered with NaHCO$_3$.

For reasons of solubility, polar solvents, for example dimethyl acetamide, dimethyl formamide, dimethyl sulfoxide, phosphoric acid tris(dimethyl amide) or N-methyl-pyrrolidone, are suitable as solvents in the process of the invention.

The synthesis can be carried out at a temperature in the range from −10° C. to and room temperature. The reaction is preferably started at about 0° C. and the temperature is then allowed to rise to room temperature.

As a condensing agent dicyclohexyl carbodiimide (DCC), which is readily accessible, is preferred, although other carbodiimides, for example 1-cyclohexyl-3-(2-morpholinoethyl)-carbodiimide toluene sulfonate or 1-ethyl-3-(3-dimethylaminopropyl)-carbodiimide hydrochloride, can also be used.

Peptides protected by the dinitrophenyl radical at the imidazole ring of the histidine are first obtained as intermediates. This dinitrophenyl radical can be split off by methods known in peptide chemistry, for example by thiolysis (Biochem.-Biophys. Res. Commun. 29, 178 (1967); Biochemistry 9, 5122 (1970)) or by hydrazinolysis (Tetrahydron Letters 44, 4121 (1971)).

In general, the Dnp-containing intermediate need not be isolated. After the peptide coupling, a thiol, for example mercaptoethanol or ethylmercaptan, or hydrazine, is added to the reaction mixture and after splitting off of the Dnp radical, which can be readily ascertained by thin layer chromatogram, the mixtue is worked up. If hydrazine is used as deblocking reagent, dimethyl formamide is unsuitable as a solvent for it is not stable with respect to hydrazine.

It is known that LH-RH and the analogs thereof can be produced especially by combining ⌐Glu-His-OH with appropriate peptides by mean of DCC with the addition of N-hydroxy-compounds reducing racemization, for example N-hydroxysuccinimide (HONSu), 1-hydroxybenzotriazole (HOBt), 3-hydroxy-4-oxo-3,4-dihydro-1,2,3-benzotriazine (HOObt), or N-hydroxy-5-norbornene-endo-2,3-dicarboximide (HNOB) (cf. Biochem-Biophys.Res.Commun 45, 767–773 (1971)).

High pressure liquid chromatography (HPLC) has revealed, however, that in this process a partial racemization of the histidine cannot be avoided (cf. Tables 1 and 2). For reducing the racemization of the histidine in the synthesis of histidine peptides, the protection of the imidazole ring by the tosyl group (Tos group) is recommended in literature. A corresponding protection by the 2,4-dinitrophenyl group (Dnp-group) appears to be unsuitable because of too great a racemization of the histidine and the tendency to further contamination (cf. Rec.Trav.Chim.Pay-Bas 93, 256 (1974)).

It has, therefore, been surprising that the racemization of the histidine can be reduced to less than 2% of D-histidine when the histidine in the starting compound ⌐Glu-His-OH is protected by the N$^{im}$-2,4-dinitrophenyl group (Dnp) and the reaction is carried out under the conditions of the invention. Under the same conditions, racemization could not be reduced below 5% of D-histidine using the tosyl group for N$^{im}$ protection.

Comparative tests in the LH-RH synthesis using different carboxy components and various condensation methods are indicated in Table 1. In the tests the content of [D-His$^2$]-LH-RH is determined by high pressure liquid chromatography (HPLC). The Table shows that only the use of DCC-HOObt and the N$^{im}$-Dnp-protection make it possible to repress racemization to a value below 2% of D-histamine.

The same results are obtained in the synthesis of a LH-RH analog as can be seen from Table 2.

TABLE 1

Study of racemization in the LH-RH synthesis

The reaction conditions are specified in Examples 3 to 5. HPLC: column (0.4×25 cm filled with Li-Chrosorb$^{(R)}$ SI 60 (silica gel of an average pore width of 60 Å) of Messrs. Merck, Federal Republic of Germany; eluant 310 parts by volume of chloroform, 190 parts by volume of methanol, 14 parts by volume of water, 3.1 parts by volume of triethylamine and 1 part by volume of formic acid; elution rate 1 ml/minute; R$_T$ (LH-RH)=about 14.0 to 14.5 minutes R$_T$ ([D his$^2$]LH-RH)=about 17.5 to 18 minutes

| carboxy component | method | % [D-His$^2$] LH—RH |
|---|---|---|
| ⌐Glu—His—OH | DCC/HOBt | 23 |
| " | DCC/HONB | 15 |

-continued

| carboxy component | method | % [D-His²] LH—RH |
|---|---|---|
| " | DCC/HONSu | 15 |
| " | DCC/HOObt | 12 |
| ⌐Glu—His(Tos)—OH | DCC/HONSu | 9 |
| " | DCC/HOObt | 5 |
| " | DCC/HOBt | 25 |
| ⌐Glu—His(Dnp)—OH | | |
| " | DCC/HONB | 7 |
| " | DCC/HONSu | 6 |
| " | DCC/HOObt | 1-2 |

TABLE 2

Study of racemization in the synthesis of
[D-Ser(Bu$^t$)$^6$]LH-RH-(1-9) nonapeptide ethylamide The reaction conditions are specified in Examples 6 and 7. HPLC: column (0.4×25 cm) filled with Li-Chrosorb$^{(R)}$SI 60 of Messrs. Merck; eluant: 410 parts by volume of acetonitrile, 29 parts by weight of methanol, 29 parts by volume of water, 20 parts by volume of chloroform, 3.7 parts by volume of triethylamine, 1 part by volume of formic acid; elution rate: 2 ml/minute; R$^T$ ([D-Ser(Bu$^t$)$^6$]-LH-RH-(1-9)-nonapeptide ethyl amide)=40 minutes, R$_T$ ([D-His², D-Ser(Bu$^t$)$^6$]LH-RH-(1,9)-nonapeptide ethyl amide)=48 minutes

| carboxy component | method | % D-His² compound |
|---|---|---|
| ⌐Glu—His—OH | DCC/HOBt | 20 |
| " | DCC/HONSu | 11 |
| " | DCC/HONB | 11 |
| " | DCC/HOObt | 6 |
| ⌐Glu—His(Dnp)—OH | DCC/HOBt | 12 |
| " | DCC/HONSu | 4 |
| " | DCC/HONB | 3 |
| " | DCC/HOObt | 1-1.5 |

The following examples illustrate the invention.

EXAMPLE 1

Preparation of ⌐Glu-His(Dnp)-OH.0.5 H$_2$O 30 g (100 mmols) of ⌐Glu-His-OH.H$_2$O and 20 g (238 mmols) of NaHCO$_3$ are dissolved in 200 ml of water and, while stirring, a solution of 22.3 g (120 mmols) of 2,4-dinitrofluorobenzene in 100 ml of dioxane is added dropwise over a period of 1 hour. Stirring of the mixture is continued for 3 hours at room temperature. The precipitate formed is filtered off with suction and the filtrate is extracted twice, each time with 200 ml of ethyl acetate. The aqueous phase is concentrated, the residue is dissolved in 200 ml of water and 120 ml of 1 N HCl are added. The upper layer is separated by decantation from the precipitating red oil and filtered. 300 ml of n-butanol are added to the aqueous solution, the mixture is thoroughly shaken and the phase mixture is left to stand overnight at 4° C. On the following day the yellow precipitate is filtered off with suction and washed with a small amount of n-butanol. For a quantitative removal of ⌐Glu-His-OH still present the precipitate is stirred twice at room temperature, each time for one hour with 300 ml of water, the mixture is filtered with suction and the residue is dried over P$_2$O$_5$ under reduced pressure. Yield: 20 g; melting point 235 to 241° C. with decomposition.

$[\alpha]_D^{21} = -12.2°$ C. (c=1, in acetic acid)
$[\alpha]_D^{21} = +18.9°$ C. (c=1, in dimethyl formamide)

EXAMPLE 2

Preparation of ⌐Glu-His(Tos)-OH as comparative substance for Table 1

3 g (10 mmols) of ⌐Glu-His-OH and 2.3 g of NaHCO$_3$ are dissolved in 20 ml of water and, while stirring at room temperature, a solution of 2.1 g (10% excess) of p-toluene sulfochloride in about 10 ml of dioxane is slowly added drop by drop. When the addition is terminated, stirring of the mixture is continued for a further hour, whereupon it is extracted twice with ether. The aqueous phase is acidified to pH 2 with 2 N HCl and the precipitate is filtered off with suction. It is washed with water and the filer residue is dried over P$_2$O$_5$ under reduced pressure. Yield 2.2 g.

EXAMPLE 3

Synthesis of LH-RH with ⌐Glu-His-OH using the different coupling methods as indicated in Table 1

640 mg of H-Trp-Ser-Tyr-Gly-Leu-Arg-Pro-Gly-NH$_2$ ditosylate and 150 ml of ⌐Glu-His-OH.H$_2$O are dissolved in 3 ml of dimethyl acetamide. 0.065 ml of N-ethylmorpholine and 68 mg of HOBt (or 81 mg of HOObt or 90 mg of HONB or 57 mg of HONSu) are added to the solution. The mixture is coold to 0° C., 110 mg of DCC are added, the whole is stirred for 1 hour at 0° C. and then overnight at room temperature. On the following day 0.1 ml of hydrazine hydrate is added, the mixture is stirred for 2 hours at room temperature and then filtered off with suction. The filtrate is partitioned between 30 ml of n-butanol and 30 ml of NaHCO$_3$ solution. The n-butanol phase is concentrated in a high vacuum and the residue is triturated with ether. The precipitate is filtered off with suction and dried. Next, the substance is dissolved in dilute acetic acid and the solution is chromatographed over approximately 10 ml Dowex 1×2 (acetate form). The column is eluted with water and the eluate is lyophilized. Yield 500–600 mg.

For further purification the crude LH-RH is subjected to a partition chromatography on a hydroxypropylated cross-linked dextran gel as described in Example 1e of German Auslegeschrift No. 2,438,350. Yield of pure LH-RH: about 250-300 mg.

EXAMPLE 4

Synthesis of LH-RH with ⌐Glu-His(Tos)-OH using the different coupling methods as indicated in Table 1

640 mg of H-Trp-Ser-Tyr-Gly-Leu-Arg-Pro-Gly-NH$_2$ ditosylate and 210 mg of ⌐Glu-His(Tos)-OH are dissolved in 3 ml of dimethyl acetamide. 0.065 ml of N-ethylmorpholine and 81 mg of HOObt (or 57 mg of HONSu) are added whereupon the mixture is cooled to 0° C. 110 mg of DCC are then added and the mixture is stirred for 1 hour at 0° C. and overnight at room temperature. The mixture is further worked up and purified as described in Example 3. Yield: 275 mg (or 250 mg).

EXAMPLE 5

Synthesis of LH-RH with ⌐Glu-His(Dnp)-OH using different coupling methods according to Table 1

11 g (25 mmols) of ⌐Glu-His(Dnp)-OH.0.5 H₂O and 32 g (25 mmols) of H-Trp-Ser-Tyr-Gly-Leu-Arg-Pro-Gly-NH₂.2 TosOH are dissolved in 150 ml of dimethyl acetamide. 4.07 g of HOObt (3-hydroxy-4-oxo-3,4-dihydro-1,2,3,-benzotriazine) (or 3.4 g of HOBt or 4.5 g HONB or 2.9 g of HONSu) are added, the mixture is cooled to 0° C., whereupon 3.25 ml of N-ethylmorpholine and 5.5 g of DCC are added. The mixture is stirred for 1 hour at 0° C. and then overnight at room temperature. The precipitate formed is filtered off with suction and washed with a small amount of dimethyl acetamide. 2.5 ml of hydrazine hydrate of 100% strength are added to the filtrate and the whole is stirred for 4 hours at room temperature. A black solution is formed. The peptide is precipitated with 1,250 ml of ethyl acetate. The precipitate is filtered off with suction and washed with ethyl acetate. It is then dissolved in 430 ml of methanol and the peptide is precipitated again with 1,400 ml of ethyl acetate. The precipitate is filtered off with suction, dissolved in 1,000 ml of n-butanol and shaken once with 1,000 ml of saturated NaHCO₃ solution and then with 750 ml of saturated NaHCO₃ solution. The n-butanol phase is concentrated in a high vacuum. The residue is triturated with ethyl acetate and dried. Crude yield: about 25 g. The substance is further purified as described in Example 3. Yield of pure substance: 12 to 14 g.

EXAMPLE 6

Synthesis of [D-Ser(Buᵗ)⁶]LH-RH-(1-9)-nonapeptide ethyl amide with ⌐Glu-His(Dnp)-OH using different coupling methods as indicated in Table 2

11 g (25 mmols) of ⌐Glu-His(Dnp)-OH.0.5 H₂O and 26.6 g (25 mmols) of H-Trp-Ser-Tyr-D-Ser(Buᵗ)-Leu-Arg-Pro-NH-C₂H₅.2 HCl are dissolved in 150 ml of dimethyl acetamide. 4.07 g of 3-hydroxy-4-oxo-3,4-dihydro-1,2,3-benzotriazine (HOOBt) (or 3.4 g of HOBt or 4.5 g of HONB or 2.9 g of HONSu) are added and the mixture is cooled to 0° C. Next, 3.25 ml of N-ethylmorpholine and 5.5 g of DCC are added and the mixture is stirred for 1 hour at 0° C. and overnight at room temperature. The precipitate formed is filtered off with suction and washed with 50 ml of dimethyl acetamide. 2.5 ml of hydrazine hydrate of 100% strength are added to the filtrate, whereupon the mixture is stirred for 4 hours at room temperature and then the peptide is precipitate with 1,250 ml of ethyl acetate. The precipitate is filtered off with suction and thoroughly washed with ethyl acetate. Next, the substance is dissolved in 430 ml of methanol. The peptide is precipitated again by adding 1,400 ml of ethyl acetate. The precipitate is dissolved in 1,000 ml of n-butanol and the solution is extracted once with 1,000 ml of saturated NaHCO₃ solution and then with 750 ml of saturated NaHCO₃ solution. The n-butanol phase is concentrated and the residue is triturated with ethyl acetate. The precipitate is filtered off with suction, washed with ethyl acetate and dried. Yield: 18.7 g.

For conversion into the acetate the above substance is dissolved in 50 ml of water and 5 ml of acetic acid and chromatographed over 230 ml of Dowex 1×2 (acetate form). The column is eluted with water. The fractions containing the substance are combined and lyophilized. Yield: about 15.0 g.

$[α]_D^{23} = -40°$ C. (c=1, in methanol)

The substance is further purified as described in Example 3.

Yield: about 9.5 to 11 g

EXAMPLE 7

Synthesis of [D-Ser-(Buᵗ)⁶]LH-RH-(1-9)-nonapeptide ethyl amide with ⌐Glu-His-OH using different coupling methods as indicated in Table 2

532 mg of H-Trp-Ser-Tyr-D-Ser-(Buᵗ)-Leu-Arg-Pro-NHC₂H₅.2 HCl and 150 mg of ⌐Glu-His-OH.H²O are dissolved in 3 ml of dimethyl acetamide. 0.065 ml of N-ethylmorpholine and 68 mg of HOBt (or 81 mg of HOOBt or 90 mg of HONB or 57 mg of HONSu) are added. The mixture is cooled to 0° C., 110 mg of DCC are added and the whole is stirred first for 1 hour at 0° C. and then overnight at room temperature.

The substance is further worked up and purified as described in Example 3. Yield: 104 to 207 mg.

What is claimed is:

1. A method for making LH-RH or an LH-RH analog, which method comprises reacting

in a solvent used in peptide chemistry and in the presence of 3-hydroxy-4-oxo-3,4-dihydro-1,2,3-benzotriazine and a carbodiimide, with a corresponding peptide residue of LH-RH or of an LH-RH analog, said peptide residue having a free amino group and protected carboxy groups, and then splitting off the protective dinitrophenyl group from the resulting product.

2. A method as in claim 1 wherein said protective dinitrophenyl group is split off with hydrazine.

3. A method as in claim 1 wherein said protective dinitrophenyl group is split off with a thiol.

4. The dipeptide ⌐Glu-His(DnP)-OH.

* * * * *